United States Patent
Al-Lamee et al.

(10) Patent No.: US 6,251,424 B1
(45) Date of Patent: Jun. 26, 2001

(54) WOUND DRESSING GEL

(75) Inventors: Kadem Gayad Al-Lamee, Leeds; Yousef Samih Taktak, Matlock, both of (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 09/383,643

(22) Filed: Aug. 26, 1999

Related U.S. Application Data (63) Continuation of application No. PCT/GB98/00494, filed on Mar. 5, 1998.

(30) Foreign Application Priority Data

Mar. 7, 1997 (GB) .................................................. 9704807

(51) Int. Cl.$^7$ ....................................................... A61K 9/70
(52) U.S. Cl. ............................................ 424/443; 424/488
(58) Field of Search .................................... 424/443, 409, 424/411, 488

(56) References Cited

U.S. PATENT DOCUMENTS

| | | |
|---|---|---|
| 4,226,232 | 10/1980 | Spence . |
| 4,292,972 | 10/1981 | Pawelchak et al. . |
| 4,582,865 | 4/1986 | Balazs et al. . |
| 4,618,491 | 10/1986 | Kanematu et al. . |
| 4,956,350 | 9/1990 | Mosbey . |
| 5,073,202 | 12/1991 | Wallach . |
| 5,089,606 | 2/1992 | Cole et al. . |
| 5,460,957 | 10/1995 | Hiura et al. . |

FOREIGN PATENT DOCUMENTS

| | | |
|---|---|---|
| 0207 022 | 12/1986 | (EP) . |
| 0112852 | 6/1988 | (EP) . |
| 0272 149 | 6/1988 | (EP) . |
| 0206 692 | 12/1988 | (EP) . |
| 0302 536 | 2/1989 | (EP) . |
| 0567 311 | 10/1993 | (EP) . |
| 0666 081 | 8/1995 | (EP) . |
| 696608 | 9/1953 | (GB) . |
| 2124487 | 2/1984 | (GB) . |
| 2255705 | 11/1992 | (GB) . |
| WO 84/00111 | 1/1984 | (WO) . |
| WO 91/04674 | 4/1991 | (WO) . |
| WO 92/16245 | 10/1992 | (WO) . |
| WO 93/10158 | 5/1993 | (WO) . |
| WO 95/03786 | 2/1995 | (WO) . |
| WO 95/17166 | 6/1995 | (WO) . |
| WO 96/10106 | 4/1996 | (WO) . |
| WO 96/13282 | 5/1996 | (WO) . |
| WO 97/03710 | 2/1997 | (WO) . |

OTHER PUBLICATIONS

"Pectin" C Rolin, extract from Industrial Gums, 3$^{rd}$ Edition 1993, Chapter 10, pp. 257–293.

"A Review of Wound Healing and Dressing Materials", Michelle Choucair and Tania Phillips, extract from Wounds 1996, vol. 8, No. 5, pp. 165–172.

"Embryogenesis, Repair and Tumorigenesis as defined by a Conserved Extracellular Matrix, Part 1", D L Evans and I Hopkinson, extract from Wounds 1996, vol. 8, No. 5 pp. 173–182.

"A new Hydrogel Would Dressing for the Treatment of Open Wounds", E Fowler and J C Papen, extract from Ostomy/Wound Management Nov./Dec. 1991 vol. 37 pp. 39–45.

"Stenting of coronary arteries. Are we the sorcerer's apprentice" P W Serruys, K J Beatt and W J van der Giessen, extract from European Heart Journal 1989 10, pp. 774–782.

Primary Examiner—Thurman K. Page
Assistant Examiner—P. E. McQueeney
(74) Attorney, Agent, or Firm—Nixon & Vanderhye (57) ABSTRACT

A gel for use in dressing a wound and a process for the manufacture of a gel are disclosed. The gel comprises a monovalent salt of a polygalacturonic, acid derivative (such as sodium pectate) a carboxy-polysaccharide (such as a monovalent salt of a carboxycellulose derivative or a monovalent salt of an alginic acid derivative) and multivalent ions providing ionic cross-links between the monovalent salt and the carboxy-polysaccharide.

23 Claims, 7 Drawing Sheets

WOUND DRESSING GEL

This is a continuation of PCT application PCT/GB98/00494, filed Mar. 5, 1998, the entire content of which is hereby incorporated by reference in this application.

FIELD OF THE INVENTION

The present invention relates to a gel for use in dressing a wound and to a process for making a gel.

BACKGROUND

Hydrogels are known for the treatment of cuts, abrasions, burns and similar wounds and consist of a matrix of polymers with a water content of up to 96%. Known hydrogel dressings exhibit less than ideal adherence characteristics and need to be covered with a secondary dressing, and the fluid or bacterial permeability of the gel depends upon the nature of the dressing used. Hydrogels are absorbent and semi-transparent and prior to application they may be refrigerated, such that the cooling effect contributes to the relief of pain.

A hydrogel for use as a wound dressing is described in International Patent Publication No. WO 92/16245, consisting of a water insoluble, water swellable cross-linked cellulose derivative, water and a polyol component. The gel described in this publication is primarily directed to the removal of necrotic tissue, as it reduces the need for the use of a chemical debriding agent or surgical excision. Thus, the known gel provides a dressing which can combine the actions of debriding and cleansing, independent upon the extent of necrosis. Furthermore, the dressing is capable of breaking down necrotic tissue and retaining resultant debris.

However, a problem with known hydrogels, for application as wound dressings, is that their adherency tends to be less than ideal. Furthermore, there is a tendency for these known compounds to disintegrate in the wound and to cause maceration to the skin around the wound.

SUMMARY OF THE INVENTION

According to a first aspect of the present invention, there is provided a gel for use in dressing a wound, comprising a monovalent salt of a polygalacturonic acid derivative, another carboxy-polysaccharide and multivalent ions providing ionic cross-links between said monovalent salt and said other carboxy-polysaccharide.

Preferably, the salt of polygalacturonic acid derivative is sodium pectate. Preferably, the cart)oxy-polysaccharide is a monovalent salt of a carboxycellulose derivative, or a monovalent salt of an alginic acid derivative.

In a preferred embodiment, the salts include ions of sodium, potassium or ammonium.

Preferably, said carboxy-polysaccharide is sodium carboxymethylcellulose, or sodium alginic, acid.

According to a second aspect of the present invention, there is provided a process for making a gel, comprising steps of: preparing a solution including a water soluble salt of a polygalacturonic acid derivative and a water soluble salt of another carboxy-polysaccharide; preparing a cross-linking agent in the form of a solution; and blending said solution of cross-linking agent with said water soluble salts to form a gel by effecting formation of ionic bonds between said salts.

DETAILED DESCRIPTION OF THE PREFERRED EMBODIMENTS

The invention will now be described by way of example only with reference to the previously identified drawings.

Figure 1:
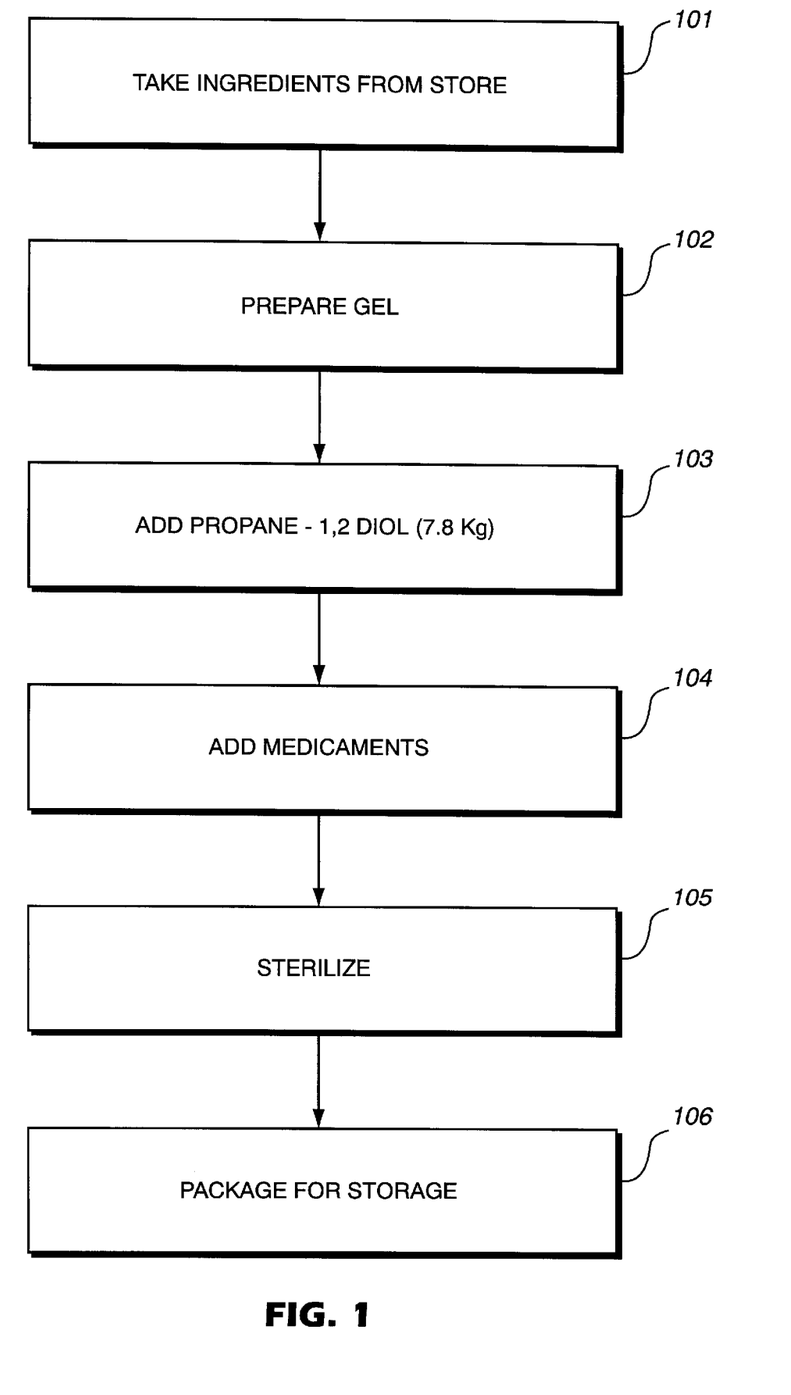
FIG. 1 shows an overview for the preparation of a hydrogel, including a gel preparation step.

An overview for the preparation of a hydrogel is shown in FIG. 1. Initially, ingredients are required or taken from store at step 101, whereafter at step 102 a gel is prepared. At step 103 propane-1,2 diol is added to the gel to enhance its physical characteristics and to act as a preservative. Optionally, thereafter and as indicated at step 104, further medicaments may be added for particular applications. At step 105 the gel is sterilised by being maintained at a temperature of 121° C. for a duration of at least twenty minutes. Thereafter, at step 106, the gel is packaged for subsequent application within a medical environment.

Figure 2:
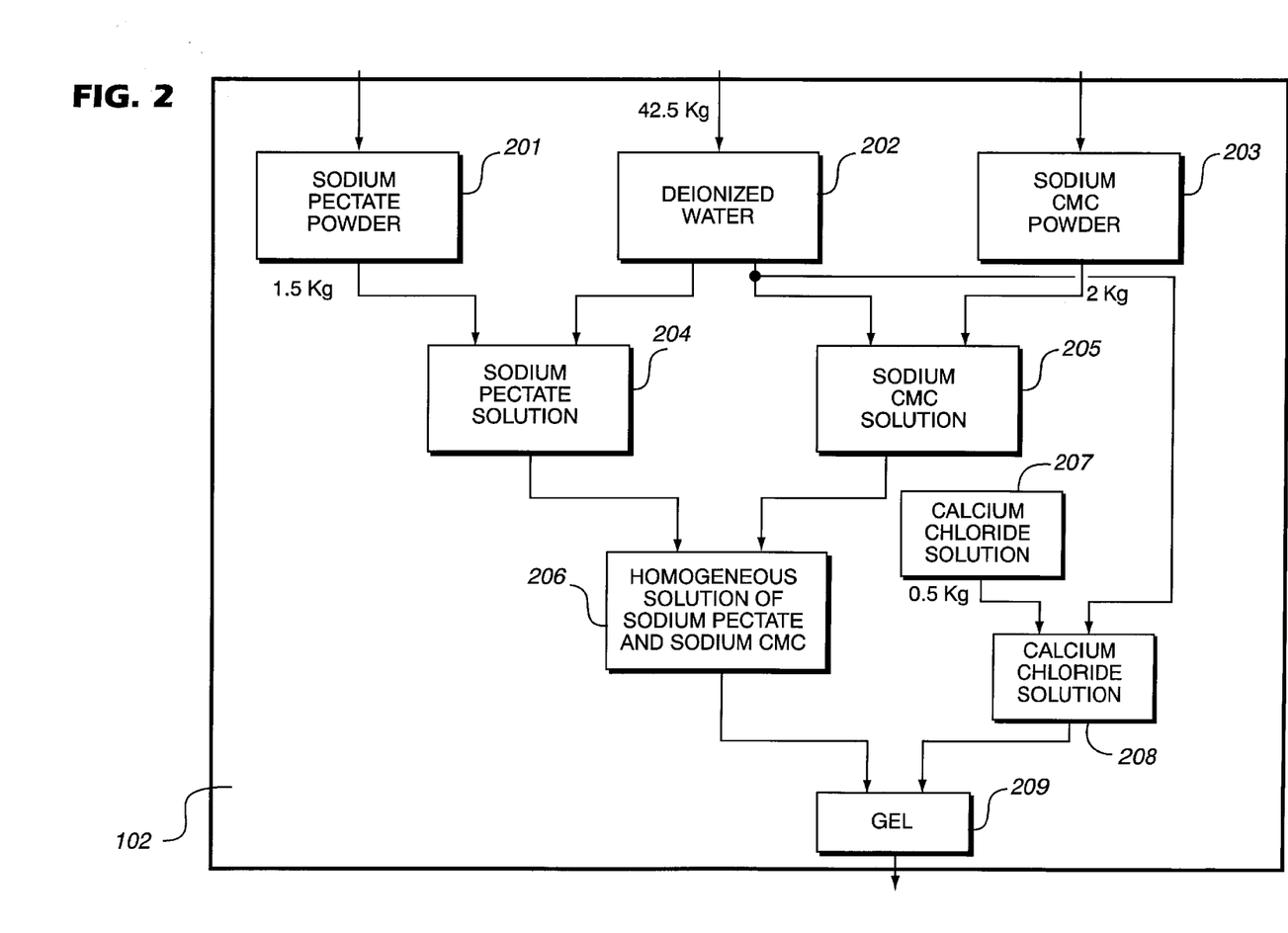
FIG. 2 details the gel preparation step identified in FIG. 1, including the preparation of sodium pectate solution and the preparation of sodium carboxymethylcellulose solution.

Step 102 for the preparation of the gel is detailed in FIG. 2. Amounts described relate to a typical batch and may clearly be scaled during the manufacturing process to result in appropriate amounts being made. The amounts illustrated in FIG. 2 require 7.8 kilograms (7.5 liters) of propane-1,2 diol being added at step 103, as illustrated in FIG. 1.

The gel produced at step 102 essentially consists of a first carboxy-polysaccharide cross-linked with a second carboxy-polysaccharide, wherein the cross-linking is facilitated by the presence of multivalent ions, In the preferred embodiment, the preparation of which is illustrated in FIG. 2, the first carboxy-polysaccharide is sodium pectate and the second carboxy-polysaccharide is sodium carboxymethylcellulose. Sodium pectate suitable for the invention is for example supplied by Citrus Colloids Limited wherein no specific trade name is available, the compound interchangeably being called sodium pectate, sodium polypectate or sodium polygalacturonate. Similarly, suitable sodium carboxymethylcellulose powder is supplied by Hercules Limited under the Trade Name "Blanose Cellulose Gum", type 7H3SXF. 1.5 kilograms of sodium pectate powder 201 are dissolved in deionised water 202 to produce sodium pectate solution 204. A similar solution is made from 2 kilograms of sodium carboxymethylcellulose powder 203 to produce sodium carboxymethylcellulose solution 205. Deionised water is also added to 0.5 kilograms of calcium chloride powder 207 to produce calcium chloride solution 208, where the total weight of deionised water used for solutions 204, 205 and amounts to 42.5 kilograms.

The sodium pectate solution 204 is mixed with the sodium carboxymethylcellulose solution 205 to produce a homogeneous solution shown at 206. The gel is then produced at 209 by adding, in a stepwise process with continual mixing, the calcium chloride solution 208, resulting in the establishment of cross-linkages produced by ionic bonding. Thus, in the preferred embodiment, the sodium ions of the carboxy-polysaccharides are attracted to the chloride ions of the calcium chloride to produce sodium chloride with the bivalent calcium ions attracting the carboxy groups of different and/or like polymers, thereby producing the ionic cross-linkages. The carboxy-polysaccharide salts are monovalent and may be sodium, potassium or ammonium for example. In the preferred embodiment as described above, sodium is the preferred salt.

In the above preferred embodiment the amount of cross-linking agent used is such that the gel exhibits characteristics suitable for adherence to a highly exudating wound. Reducing the amount of said agent produces gets of successively lower viscosity which are suitable for different applications and practices. For example in some countries less viscous gels are preferred for treatment of deep highly exudating wounds and thus a gel according to the present invention which is suitable for these requirements can be made by reducing the amount of cross-linking agent used.

Incorporation of additional medicaments as described is facilitated in the invention through carboxy groups that are not incorporated into cross-linked ionic bonds. This is in addition to the simple trapping of said medicaments in the gel matrix. These medicaments may consist of an anti-bacterial agent, an anti-fungal agent, an anti-mycotic agent, an anesthetic, an additional debriding agent or an anti-inflammatory agent. Alternatively, other agents may be added, such as a growth factor, an enzyme such as Lysozyme or a proteinase and nutrients such as vitamins, amino acids or trace elements. For example, it is known that the addition of zinc ions may be beneficial to assist in the healing process.

Figure 3:
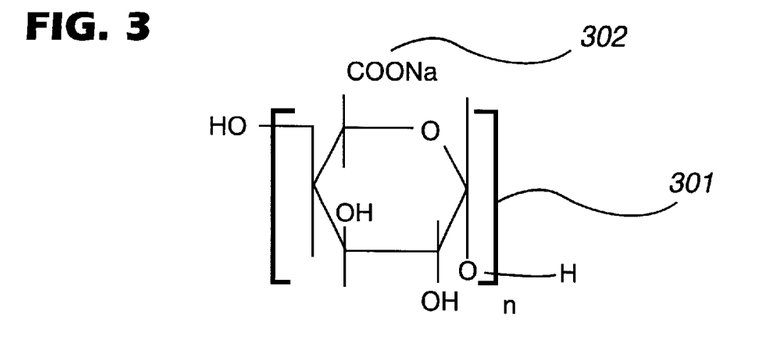
FIG. 3 details a sodium pectate polymer.

A sodium pectate polymer molecule is illustrated in FIG. 3, in which the unit bounded by braces 301 is repeated to produce the polymer chain, typically consisting of more than 100 monomer units. Each monomer unit includes a sodium carboxy group 302 and it is the process of replacement of the sodium atoms of these groups which presents an ionised component for cross-linking with other polymer molecules.

A sodium carboxymethylcellulose polymer is shown in FIG. 4, where again the repeating monomer is enclosed with braces 401. Each repeating monomer section includes cyclic components with each said component incorporating a sodium carboxymethyl group extending from each cyclic group. Again, some of the sodium atoms are removed thereby ionising the monomer units to facilitate the creation of cross-bonds with other polymers.

Figure 5:
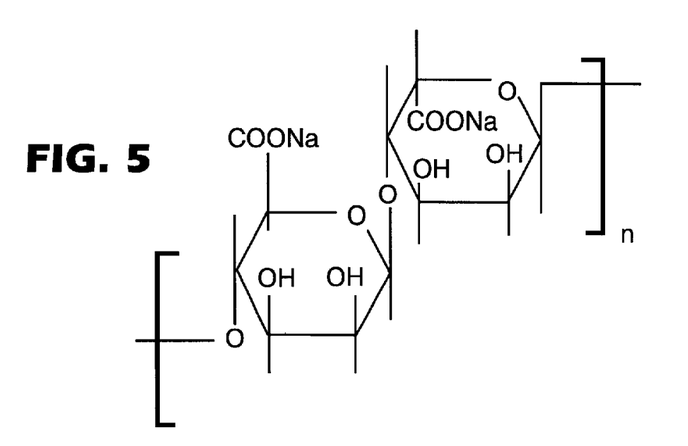
FIG. 5 details a sodium alginic acid polymer.

A sodium alginic acid polymer is shown in FIG. 5, again having sodium caboxy groups from which a sodium atom may be removed to facilitate the creation of ionic cross-bonding.

Figure 4:
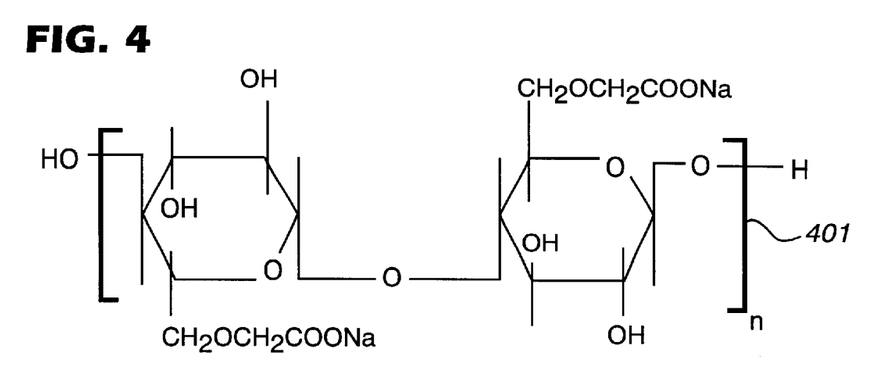
FIG. 4 details a sodium carboxymethylcellulose polymer.
Figure 6:
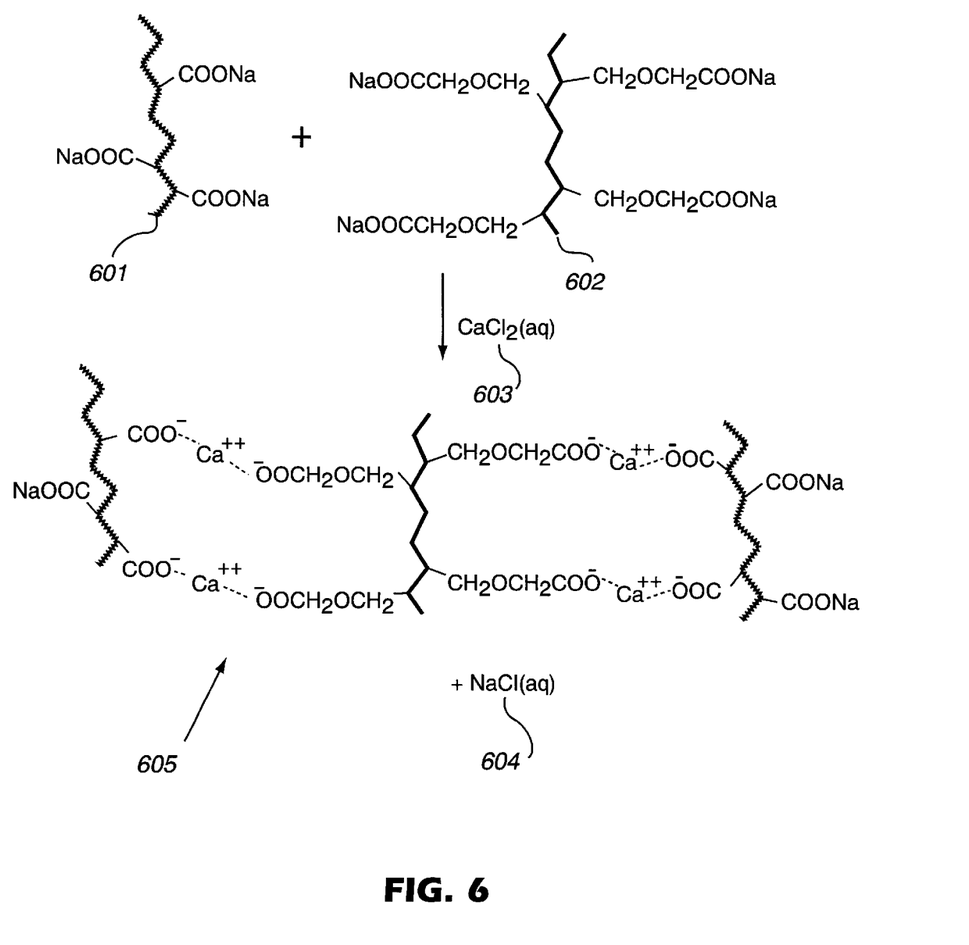
FIG. 6 illustrates the formation of cross-linkages between the polymers illustrated in FIGS. 3 and 4, when reacted with calcium chloride.

The formation of cross-bonds or links between a sodium pectate polymer of the type shown in FIG. 3 and a sodium carboxymethylcellulose polymer, of the type shown in FIG. 4, is illustrated in FIG. 6. Sodium pectate polymers 601 are placed in solution with sodium carboxymethylcellulose polymers 602. Aqueous calcium chloride 603 is added thereby placing calcium and chloride ions into the solution containing both sodium pectate and sodium carboxymethylcellulose polymers. The sodium ions present within the original polymers 601 and 602 are attracted to the chloride ions to produce aqueous sodium chloride 604, with the resulting free carboxy groups of the two polymers being attracted to the bivalent calcium ions. However, given that two carboxy groups are required in order to balance with each calcium ion, cross-linkages are formed between adjacent polymer strands, resulting in the production of the cross-lined hydrogel 605.

Figure 7:
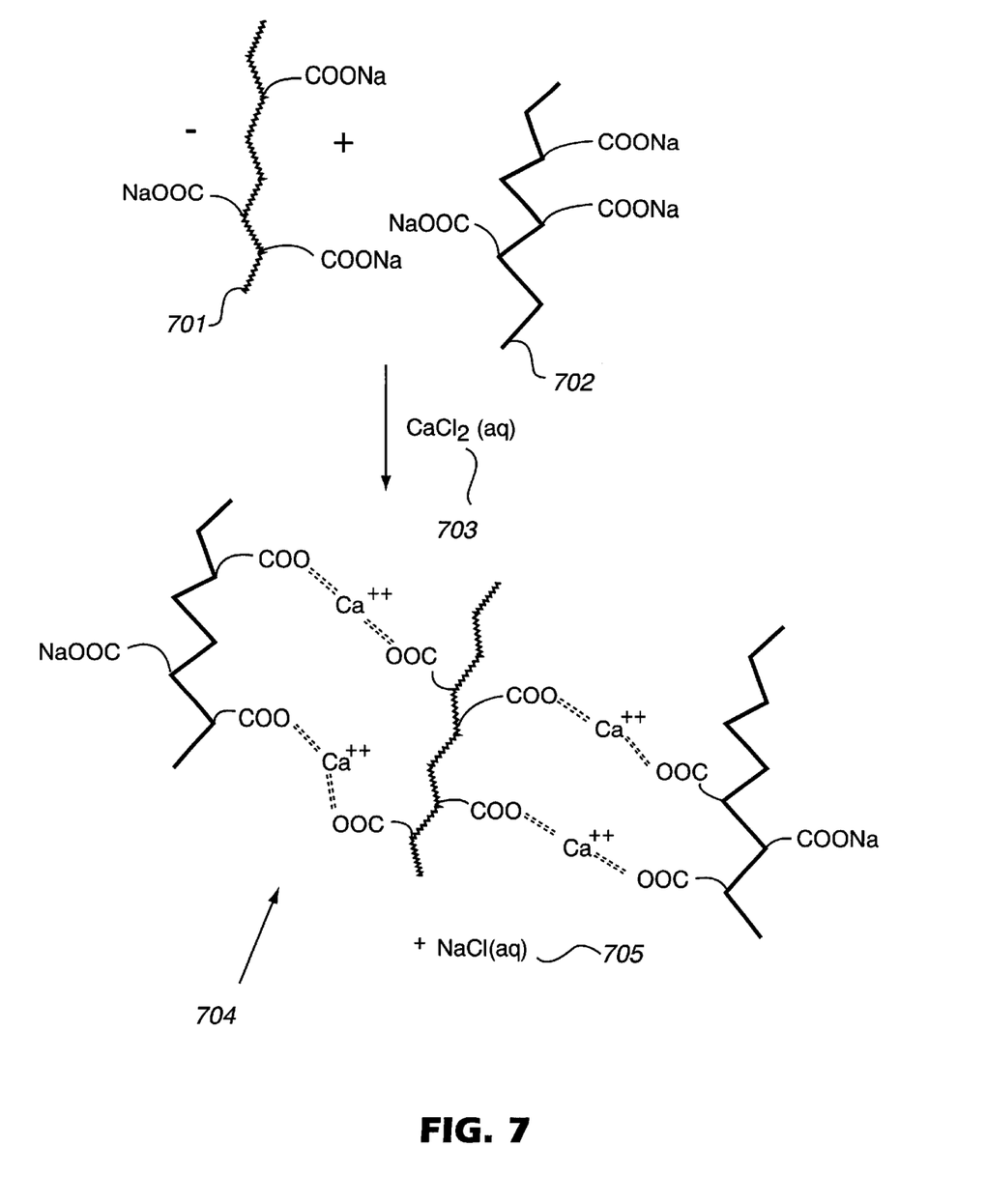
FIG. 7 illustrates the formation of cross-linkages between the polymers illustrated in FIGS. 3 and 5, when reacted with calcium chloride.

A similar reaction is shown in FIG. 7 in which a sodium alginic acid polymer 702, functionally similar to polymer 602, reacts with a sodium pectate polymer 701, Again, aqueous calcium chloride 703 is added, resulting in the substitution of the monovalent sodium ions for bivalent calcium ions to produce an alternative cross-linked hydrogel 704 and sodium chloride 705.

Figure 8:
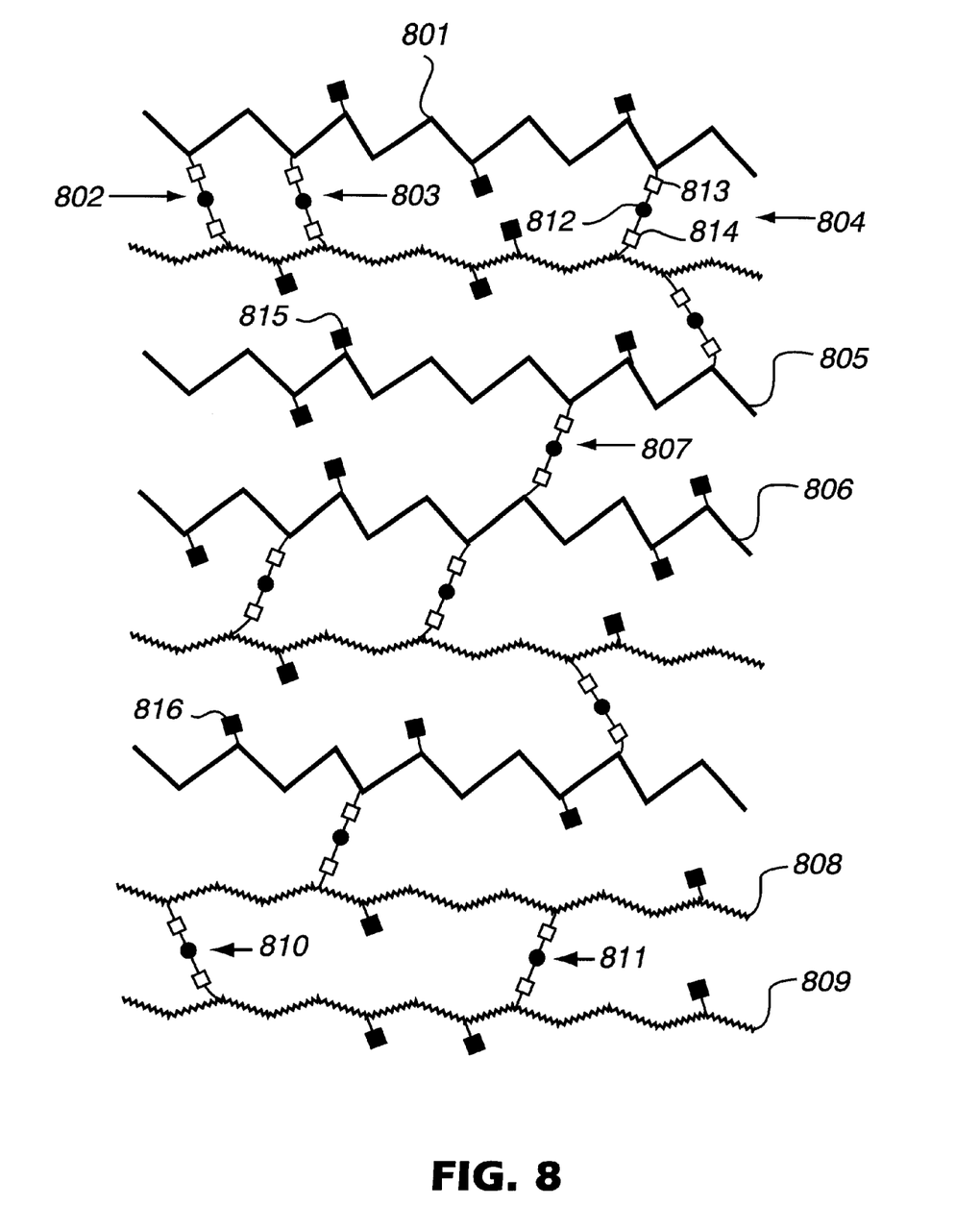
FIG. 8 illustrates, in two dimensions, a portion of gel composed of cross-linked polymers as detailed in FIG. 6 or FIG. 7.

A cross-linked hydrogel 605 is also shown in FIG. 8. As shown in FIG. 8, each polymer such as polymer 801 for example, may include a plurality of ionic cross-linkages and the total number of cross-linkages (802, 803 and 804 for polymer 801) within the gel will influence the viscosity of the gel, which, as previously stated, may be adjusted to satisfy particular medical applications and preferences.

The reactions shown in FIG. 6 and FIG. 7 consist of a first carboxy-polysaccharide forming a cross-linkage with a second carboxy-polysaccharide. However, as shown in FIG. 8, cross-linkages are also formed between carboxy-polysaccharides of the same type. Two sodium carboxymethylcellulose polymers, 805 and 806 have a cross-link 807 and similarly, two sodium pectate polymers 808 and 809 have two cross-links 810 and 811. As described above a cross-link such as cross-link 804 comprises a calcium ion 812 and two carboxy groups 813 and 814, one group being supplied from each polymer. Each caboxy-polysaccharide should have at least one link to another carboxy-polysaccharide and it is not necessary for all of the potential bonding sites to be exploited. Two unused potential bonding sites (sodium carboxy group) include 815 and 816 for example.

This in turn facilitates the possibility of other groups being bound using a similar mechanism. However, not all of the bonding sites should be exploited for cross-linking otherwise there is a tendency for the gel to become hard and brittle.

The packaged get identified at step 106 may be kept in storage for a period in the region of two years, provided that storage temperatures do not exceed 25° C.

Figure 9:
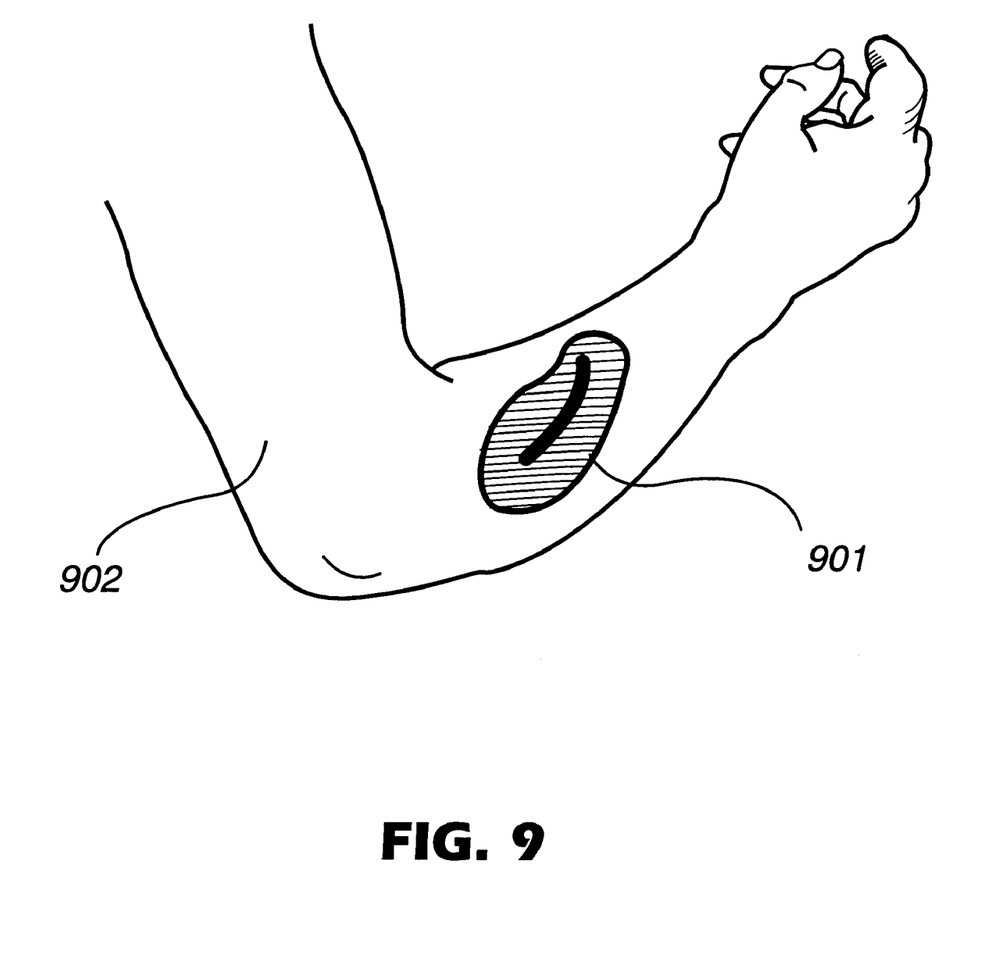
FIG. 9 illustrates the application of the gel produced by the process shown in FIG. 1 applied to a wound.

The gel is particularly useful for application to relatively deep wounds, of the type illustrated at FIG. 9. Wounds 901, in this example taking the form of a severe and deep dermal ulceration in a patients arm 902 are often highly exudating or dry. The gel is therefore applied into the wound in order to prevent or at least reduce the amount of fluid oozing out of the wound site if highly exudating or to donate fluid if the wound is dry, and primarily to assist in the healing of the wound, aid removal of unwanted matter and to facilitate the prevention of undesirable contamination. Other wound categories applicable to this gel include, but are not restricted to, Stage I, II or III pressure ulcers, dermal ulcers, donor sites, second degree burns, abrasions, blisters and, chronic wounds.

Prior to application of the dressing, the wound itself is irrigated with sterile saline solution, whereafter excess liquid is removed by an antiseptic swab. Gel, which may have been stored in a tube or sachet etc is squeezed into the wound to a minimum depth of 5 mm, whereafter any excess gel is discarded. The tendency of the gel is to adhere to the wound, but it is necessary to apply a secondary dressing so as to maintain a moist, infection free environment. A further advantage of the invention is that the gel maintains structural integrity and thus does not readily disintegrate in environments such as highly exudating wounds. Removal of the dressing is simple and is facilitated by the fact that the dressing remains intact.

The tendency of the gel will be to remove excess liquid from its environment while ensuring that the environment does rot dry cut and thus remains moist. If the wound site is or becomes dry, the gel will tend to donate liquid to its environment ensuring that an equilibrium is maintained between the gel itself and its surrounding tissue.

The example given in the description of this embodiment concerning the proportions of the mixture may be varied to suit particular applications. In general, the carboxy-polysaccharide components, such as sodium pectate and sodium carboxymethylcellulose in the preferred embodiment, comprise at least 0.1% by weight of the total weight of the packaged gel.

The production process as descried herein involves reactions and processes which take place at normal ambient temperatures. However, in some applications, it may be desirable to apply additional heating and/or other methods to the system in order to improve production times, An important advantage of the process described for making a gel according to the invention is that the carboxy-polysaccharides used as starting materials are water soluble. This facilitates mixing of components which in turn reduces costs in large scale processing.

The present invention is further illustrated by the following example of laboratory scale synthesis. A gel of the invention having the following composition was made:

| Material | Weight | % by Weight |
|---|---|---|
| Sodium pectate | 15 g | 2.78 |
| Sodium carboxymethylcellulose (Blanose 7H3SXF) | 20 g | 3.70 |
| Calcium chloride | 5 g | 0.93 |
| Propylene glycol (Propane-1,2 diol) | 78 g | 13.89 |
| Deionised water | 425 g | 78.70 |

15 g of sodium pectate are stirred in 200 ml of deionised water at room temperature, until fully dissolved. Similarly, 20 g of sodium carboxymethylcellulose are stirred in 200 ml of deionised water, until fully dissolved. The two solutions are then mixed together until a homogeneous solution is formed. 5 g of calcium chloride are dissolved in 25 ml of deionised water, and added stepwise to the above solution. The mix is then homogenised carefully resulting in the formation of a highly viscous gel. Finally, 75 ml of propylene glycol are added to the gel with continuous mixing, to ensure that a homogeneous gel is formed. The gel is then steam sterilised at 121° C. for twenty minutes in an autoclave.

What is claimed is:

1. A wound dressing gel comprising a water soluble monovalent salt of a polygalacturonic acid derivative, a water-soluble monovalent salt of another carboxy-polysaccharide and a wound adhering amount of non-fiber associated multivalent ions, the non-fiber associated multivalent ions providing cross-links, between said monovalent salt and said other carboxy-polysaccharide.

2. A gel according to claim 1, wherein said salt of polygalacturonic acid derivative is sodium pectate.

3. A gel according to claim 1 wherein said other carboxy-polysaccharide is a monovalent salt of a carboxycellulose derivative.

4. A gel according to claim 1, wherein said other carboxy-polysaccharide is a monovalent salt of an alginic acid derivative.

5. A gel according to claim 1, wherein said water-soluble monovalent salts include ions of sodium, potassium or ammonium.

6. A gel according to claim 1, wherein said other carboxy-polysaccharide is sodium carboxymethylcellulose.

7. A gel according to claim 1, wherein said other carboxy-polysaccharide is sodium alginate.

8. A gel according to claim 1, wherein said multivalent ions are divalent.

9. A gel according to claim 8, wherein said divalent ions are ions of calcium or magnesium.

10. A gel according to claim 1, further comprising a polyol or diol component.

11. A gel according to claim 10, wherein said polyol or said diol component includes propane-1,2 diol.

12. A gel according to claim 1, wherein said monovalent salt and said carboxy-polysaccharides collectively comprise at least 0.1% by weight of the gel.

13. A gel according to claim 1, wherein said gel is sterile.

14. A gel according to claim 1, further comprising one or more components selected from the group consisting of an antibacterial agent; an anti-fungal agent; an anti-mycotic agent; an anesthetic; an additional debriding agent; an antiflammatory agent; a growth factor; an enzyme; simple nutrients and trace elements.

15. A gel according to claim 14, wherein said enzyme is lysozyme or protanase.

16. A gel according to claim 14, wherein said simple nutrients are vitamins or amino acids.

17. A gel according to claim 14, wherein said trace elements are zinc ions.

18. A gel according to claim 14, wherein not all of the polysaccharide carboxy groups form cross-links through the non-fiber associated multivalent ions and one or more of said additional components binds to carboxy groups that do not farm cross-links with the non-fiber associated multivalent ions.

19. A process for preparing a wound dressing gel comprising the steps of:
   a) preparing an aqueous solution of a water soluble salt of a polygalacturonic acid derivative and a water soluble salt of another carboxy-polysaccharide;
   (b) preparing an aqueous solution of a wound adhering amount of non-fiber associated multivalent ions;
   (c) blending said solution of water soluble salts of said polygalacturonic acid derivative and said other carboxy-polysaccharide with said solution of non-fiber associated multivalent ions;
   whereby the non-fiber associated multivalent ions provide cross-links between said polygalacturonic acid derivative and said other carboxy polysaccharide.

20. A process according to claim 19, wherein said carboxy-polysaccharide is a monovalent salt of carboxycellulose derivative.

21. A process according to claim 19, wherein said carboxy-polysaccharide is a monovalent salt of an alginic acid derivative.

22. A process according to claim 3 herein said salt of a polygalacturonic acid derivative is sodium pectate.

23. A process according to claim 19, wherein said salt of a carboxy polysaccharide is sodium carboxymethylcellulose.

* * * * *